US012629845B2

(12) United States Patent (10) Patent No.: US 12,629,845 B2
Ohnishi et al. (45) Date of Patent: May 19, 2026

(54) CONTROL SYSTEM, CONTROL DEVICE, AND CONTROL METHOD

(71) Applicants:KEIO UNIVERSITY, Tokyo (JP); MOTION LIB, INC., Kawasaki (JP); TERUMO KABUSHIKI KAISHA, Tokyo (JP)

(72) Inventors: Kouhei Ohnishi, Tokyo (JP); Takahiro Mizoguchi, Kawasaki (JP); Shin Maki, Ashigarakami-gun (JP); Yoshiyuki Habu, Ashigarakami-gun (JP); Toshihiro Fujii, Ashigarakami-gun (JP)

(73) Assignees: KEIO UNIVERSITY, Tokyo (JP); MOTION LIB, INC., Kawasaki (JP); TERUMO KABUSHIKI KAISHA, Tokyo (JP)

( * ) Notice: Subject to any disclaimer, the term of this patent is extended or adjusted under 35 U.S.C. 154(b) by 143 days.

(21) Appl. No.: 18/553,386

(22) PCT Filed: Mar. 29, 2022

(86) PCT No.: PCT/JP2022/015720
§ 371 (c)(1),
(2) Date: Sep. 29, 2023

(87) PCT Pub. No.: WO2022/210800
PCT Pub. Date: Oct. 6, 2022

(65) Prior Publication Data
US 2024/0359335 A1 Oct. 31, 2024

(30) Foreign Application Priority Data
Mar. 30, 2021 (JP) ................................. 2021-058538

(51) Int. Cl.
*B25J 13/08* (2006.01)
*A61B 34/37* (2016.01)
(Continued)

(52) U.S. Cl.
CPC ............. *B25J 13/085* (2013.01); *A61B 34/37* (2016.02)

(58) Field of Classification Search
CPC ..... B25J 13/085; B25J 3/00; B25J 3/04; B25J 11/00; B25J 13/025; A61B 34/37
See application file for complete search history.

(56) References Cited

U.S. PATENT DOCUMENTS 5,855,553 A * 1/1999 Tajima ................... A61B 34/70
600/407
2012/0071895 A1* 3/2012 Stahler ................... A61B 34/20
606/130
(Continued)

FOREIGN PATENT DOCUMENTS

JP S6434686 A 2/1989
JP H08215211 A 8/1996
(Continued)

OTHER PUBLICATIONS

International Search Report (PCT/ISA/210) with translation and Written Opinion (PCT/ISA/237) mailed on Jun. 21, 2022, by the Japan Patent Office as the International Searching Authority for International Application No. PCT/JP2022/015720. (10 pages).
(Continued)

*Primary Examiner* — Harry Y Oh
(74) *Attorney, Agent, or Firm* — Buchanan Ingersoll & Rooney PC

(57) ABSTRACT
A control system includes a master device, a slave device, and a control device. Furthermore, the control device includes a tactile force transmission unit and a mode setting unit. The tactile force transmission unit controls tactile force transmission in the master device and the slave device. The mode setting unit changes an amplification factor of force transmitted from the slave device to the master device in a specific section in which a moving element of the slave
(Continued)

device moves on the basis of a physical quantity in the moving element of the slave device.

19 Claims, 9 Drawing Sheets

(51) Int. Cl.

| | |
|---|---|
| *B25J 1/00* | (2006.01) |
| *B25J 3/00* | (2006.01) |
| *B25J 3/02* | (2006.01) |
| *B25J 3/04* | (2006.01) |

(56) References Cited

U.S. PATENT DOCUMENTS

| | | | | |
|---|---|---|---|---|
| 2012/0245595 | A1* | 9/2012 | Kesavadas | B25J 9/1689 606/130 |
| 2014/0171964 | A1* | 6/2014 | Yang | A61B 34/37 606/130 |
| 2015/0230697 | A1* | 8/2015 | Phee | A61B 1/0057 901/41 |
| 2016/0106957 | A1 | 4/2016 | Olson et al. | |
| 2017/0333143 | A1* | 11/2017 | Yoshii | A61B 34/37 |

FOREIGN PATENT DOCUMENTS

| | | |
|---|---|---|
| JP | 2011-519286 A | 7/2011 |
| WO | 2016125385 A1 | 8/2016 |

OTHER PUBLICATIONS

Office Action (Notice of Reasons for Refusal) dated Oct. 7, 2025, in corresponding Japanese Patent Application No. 2023-511436 and English translation of the Office Action. (8 pages).

* cited by examiner

*FIG. 4*

CONTROL SYSTEM, CONTROL DEVICE, AND CONTROL METHOD

TECHNICAL FIELD

The present invention relates to a control system, a control device, a control method, and a program.

BACKGROUND ART

Conventionally, in a master-slave manipulator, a configuration for executing bilateral control such as force feedback control for applying operation reaction force corresponding to an operation load on a slave device side to an operation tool on a master device side is known (see, for example, Patent Literature 1).

CITATION LIST

Patent Literature

Patent Literature 1: JP 64-34686 A

SUMMARY OF INVENTION

Technical Problem

However, in a case where bilateral control is performed in a master-slave system, force detected by a slave device may be weaker than force actually input to the slave device.

For example, in a case where the slave device is a device in which a flexible member such as a wire is used as a moving element, force input in a thrust direction may be weakened and detected by bending of the moving element of the slave device.

In this case, there is a possibility that tactile force input to the slave device is not accurately fed back to a master device and an operator of the master device cannot perform an appropriate operation.

An object of the present invention is to transmit tactile force input from the outside to a slave device to a master device so that the tactile force can be more easily perceived.

Solution to Problem

In order to achieve the object described above, a control system according to an aspect of the present invention is a control system including: a master device to which an operation of an operator is input; and a slave device that operates in accordance with the operation input to the master device, the control system including: a control means that controls transmission of tactile force in the master device and the slave device; and an amplification factor setting means that changes an amplification factor of force transmitted from the slave device to the master device in a specific section in which a moving element of the slave device moves, on the basis of a physical quantity in the moving element of the slave device.

Advantageous Effects of Invention

According to the present invention, it is possible to transmit tactile force input from the outside to a slave device to a master device so that the tactile force can be more easily perceived.

BRIEF DESCRIPTION OF DRAWINGS

FIG. 4 is a schematic diagram illustrating a hardware configuration of an information processing device constituting the control device 30.

DESCRIPTION OF EMBODIMENTS

Hereinafter, an embodiment of the present invention will be described with reference to the drawings.

First Embodiment

[Configuration]

Figure 1:
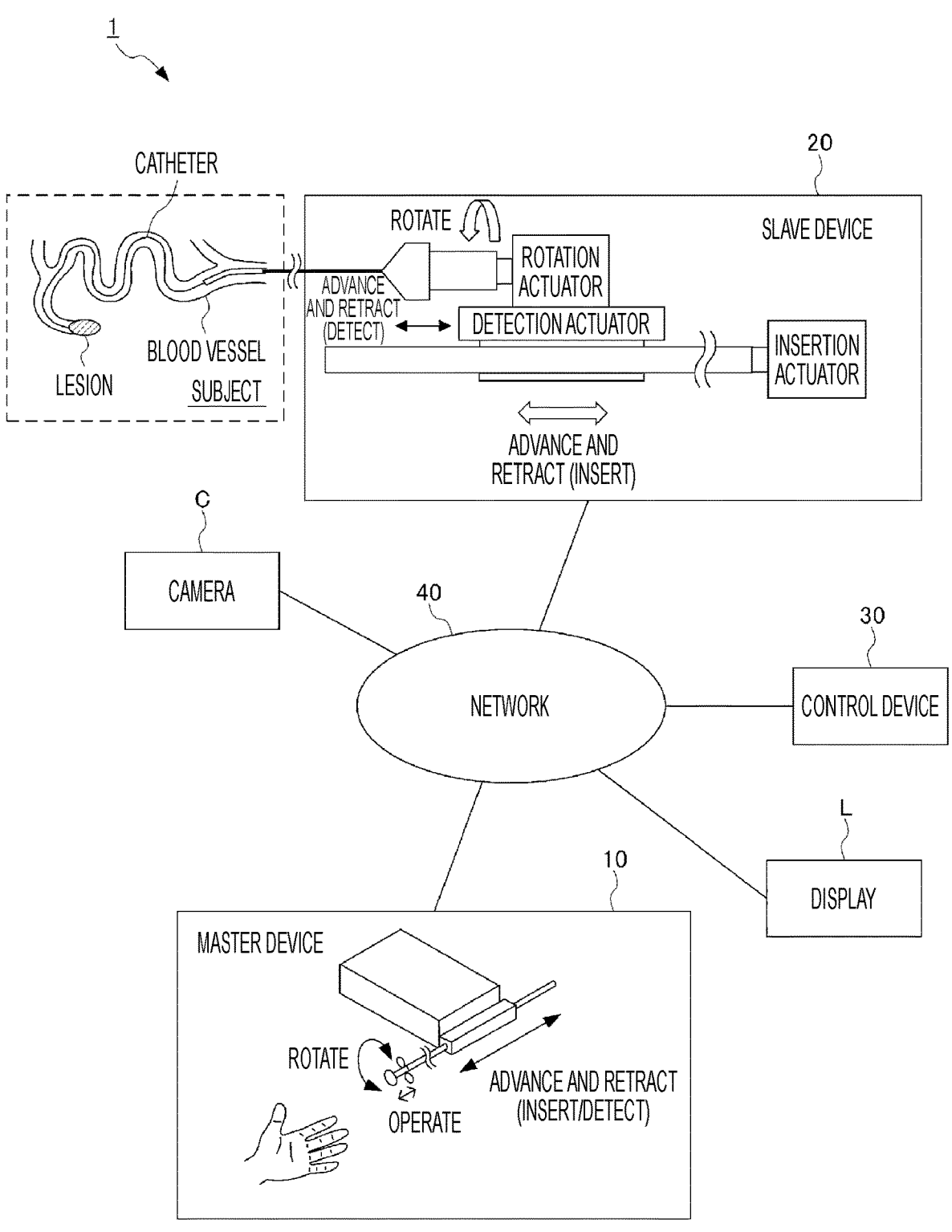
FIG. 1 is a schematic diagram illustrating an overall configuration of a control system 1 according to an embodiment of the present invention.

FIG. 1 is a schematic diagram illustrating an overall configuration of a control system 1 according to an embodiment of the present invention.

As illustrated in FIG. 1, the control system 1 according to the present embodiment is configured as a master-slave system including a master device 10 and a slave device 20 that are mechanically separated. As an example, in the control system 1 in the present embodiment, it is assumed that the master device 10 constitutes a manipulator operated by a user, and the slave device 20 constitutes a catheter system including an end effector to be inserted into a subject.

In FIG. 1, the control system 1 includes the master device 10, the slave device 20, and a control device 30, and the master device 10, the slave device 20, and the control device 30 is configured to perform wired or wireless communication via a network 40. Note that the control system 1 can appropriately include a display L and a plurality of cameras C. As the cameras C, various imaging devices such as a video camera that captures an external appearance of a subject into which the slave device 20 is inserted or an X-ray camera that captures the inside of the subject by X-ray can be used. Furthermore, it is also possible to include a plurality of displays L that displays various images captured by the plurality of cameras C.

The master device 10 receives an operation similar to an operation for a conventional catheter configured mechanically, and detects a position of a movable portion (a movable member of the manipulator, or the like) moved by the input operation. The master device 10 transmits information representing the detected position of the movable portion to the control device 30. Furthermore, the master device 10 outputs reaction force by an actuator in response to the input operation in accordance with an instruction from the control device 30.

Specifically, the master device 10 receives an operation of advancing and retracting the catheter (for example, an operation of inserting the catheter into a blood vessel, an operation of slightly moving the catheter to detect tactile force near a lesion, or the like), an operation of axially rotating the catheter (for example, an operation of changing a direction of the end effector, or the like), and an operation of operating the end effector (for example, in a case where the end effector is a balloon, an operation of expanding and contracting the balloon, and in a case where the end effector is a pair of forceps or the like, an operation of opening and closing the pair of forceps, or the like), and applies reaction force to these operations, and transmits, to the control device 30, information representing a position of the movable portion moved by each operation.

The slave device 20 drives an actuator in accordance with an instruction from the control device 30 to perform an operation corresponding to an operation input to the master device 10, and detects a position of a movable portion (a movable element of the actuator, the catheter moved by the actuator, or the like) moved by the operation. When the slave device 20 operates, various types of external force are input to the slave device 20 from an environment. As a result, the position of the movable portion in the slave device 20 indicates a result of the various types of external force acting on an output of the actuator. Then, the slave device 20 transmits information representing the detected position of the movable portion to the control device 30. Here, as the various types of external force input to the slave device 20 from the environment, there are pressing force in a direction intersecting with a thrust direction for bending the catheter, resistance force in the thrust direction received by the catheter from a blood vessel, and the like. Thus, in a case where the force in the thrust direction in the slave device 20 is simply detected (or calculated) and fed back to the master device 10, the external force input to the slave device 20 is unintended large resistance force, and thus desired tactile information cannot be transmitted. Thus, in the present embodiment, as will be described later, the force in the thrust direction detected in the slave device 20 is amplified at a predetermined amplification factor and transmitted to the master device 10, so that a user can more easily perceive the force.

The control device 30 includes, for example, an information processing device such as a personal computer (PC) or a server computer, and controls the master device 10, the slave device 20, the display L, and the cameras C. For example, the control device 30 executes control for acquiring positions of the movable portions of the master device 10 and the slave device 20 (rotation angles of the actuators detected by rotary encoders, advancing and retracting positions of the movable portions detected by linear encoders, or the like), and transmitting tactile force between the master device 10 and the slave device 20.

When operating the master device 10 and the slave device 20 as the master-slave system, the control device 30 in the present embodiment performs coordinate transformation (transformation by a transformation matrix) of parameters (input vectors) of a real space calculated on the basis of information representing the positions of the movable portions (information representing positions of movable elements of the actuators, positions of members moved by the actuators, or the like) into a virtual space in which a position and force can be handled independently. That is, coordinate transformation of the input vectors from the real space of an oblique coordinate system in which a position and force are related to each other to the virtual space of an orthogonal coordinate system in which a position and force are independent from each other is performed. The parameters calculated by the coordinate transformation represent state values of positions and force corresponding to the input vectors in the virtual space. Then, in the virtual space after the coordinate transformation, the control device 30 performs an arithmetic operation to cause the state values of the positions and the force calculated from the input vectors to follow the respective target values of the positions and the force for performing control of the positions and the force (here, transmission of tactile force), and performs inverse transformation (transformation by an inverse matrix of the transformation matrix) to return an arithmetic operation result to the real space. Moreover, the control device 30 implements the master-slave system that transmits tactile force between the master device 10 and the slave device 20 by driving each actuator on the basis of the parameters (a current command value and the like) of the real space acquired by the inverse transformation.

Furthermore, the control device 30 in the present embodiment enables, when transmitting tactile force between the master device 10 and the slave device 20, amplification of force transmitted from the slave device 20 to the master device 10 and transmission of the force so that an operator of the master device 10 can more easily perceive the tactile force. Here, in a case where the force transmitted from the slave device 20 to the master device 10 is amplified (that is, expanded) at an amplification factor larger than 1, force transmitted from the master device 10 to the slave device 20 may be amplified (that is, reduced) at an amplification factor smaller than 1. With this configuration, it is possible to suppress divergence of the control. Furthermore, in the present embodiment, when transmitting tactile force between the master device 10 and the slave device 20, the information regarding the position can be either amplified and transmitted or directly transmitted without being amplified.

Note that, since the position and a velocity (or acceleration) or an angle and an angular velocity (or angular acceleration) are parameters that can be replaced by a differential and integral operation, it is possible to appropriately replace them with the velocity, the angular velocity, or the like when processing related to the position or the angle is performed.

Figure 2:
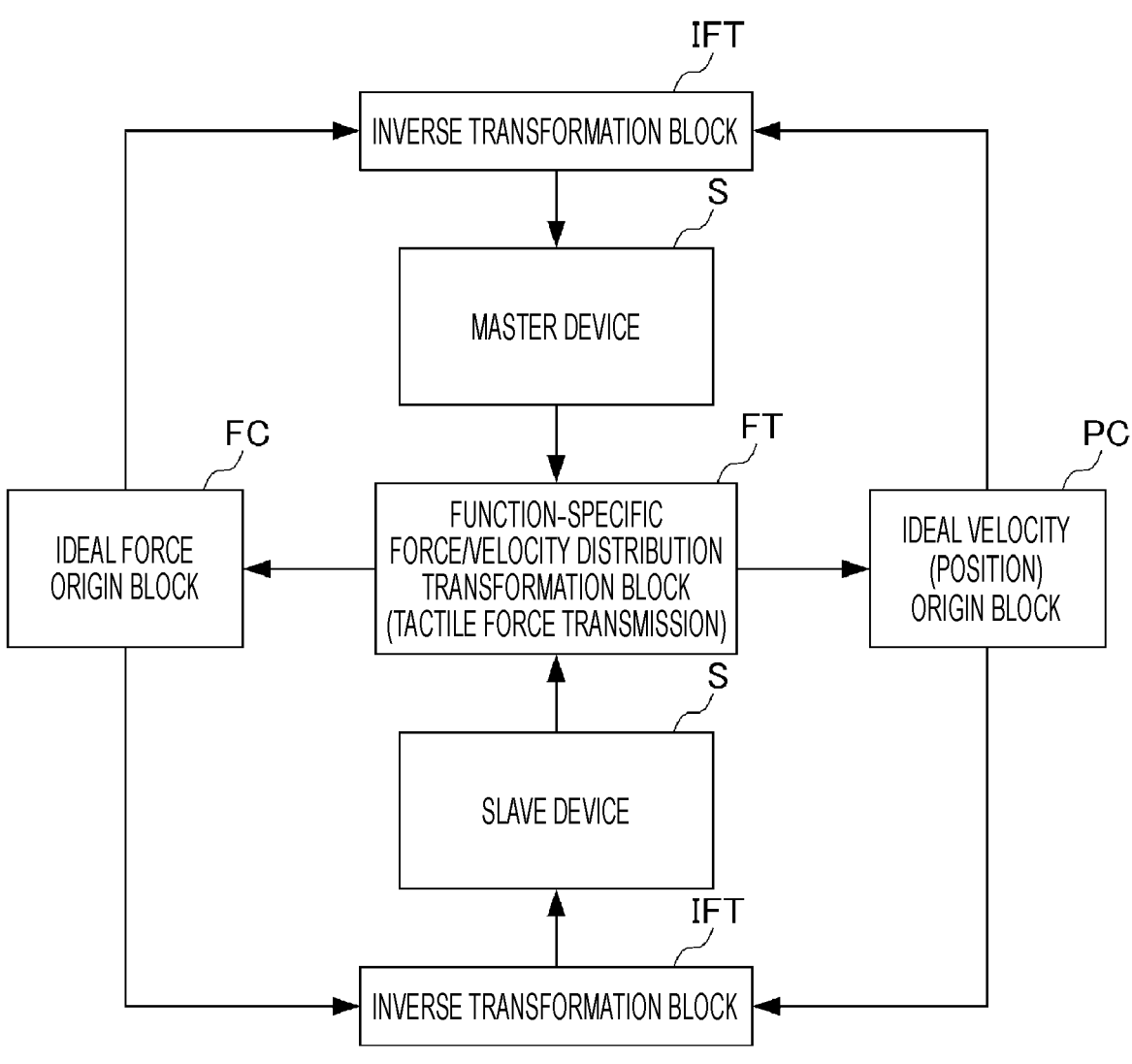
FIG. 2 is a schematic diagram illustrating a basic principle of tactile force transmission control executed by a control device 30.

FIG. 2 is a schematic diagram illustrating a basic principle of tactile force transmission control executed by the control device 30.

The basic principle illustrated in FIG. 2 is to determine an operation of the actuator by performing an arithmetic operation in at least one domain of a velocity or force with information representing a position of the movable portion (current position of the movable portion) as an input.

That is, the basic principle of the present invention is represented as control rules including a control object system S, a function-specific force/velocity distribution transformation block FT, at least one of an ideal force origin block FC or an ideal velocity origin block PC, and an inverse transformation block IFT.

The control object system S is the master device 10 or the slave device 20 including the actuator, and controls the actuator on the basis of the acceleration or the like. Here, as described above, since the acceleration, the velocity, and the position are physical quantities that can be mutually transformed by differentiation and integration, any of the acceleration, the velocity, and the position may be used for the control. Here, it is assumed that the control rules are expressed by mainly using the velocity calculated from the position.

The function-specific force/velocity distribution transformation block FT is a block that defines transformation of control energy in the domains of the velocity and the force, which is set in accordance with a function of the control object system S. Specifically, the function-specific force/velocity distribution transformation block FT defines coordinate transformation whose inputs are a value serving as a reference (reference value) for the function of the control object system S and a current position of the movable portion. The coordinate transformation is generally transformation of an input vector whose elements are a reference value and a current velocity to an output vector including a velocity for calculating a control target value of a velocity, and transformation of an input vector whose elements are a reference value and current force to an output vector including force for calculating a control target value of force. Specifically, the coordinate transformation in the function-specific force/velocity distribution transformation block FT can be generalized and represented as in the following Expressions (1) and (2).

[Math. 1]

$$\begin{pmatrix} \dot{x}_1 \\ \dot{x}_2 \\ \vdots \\ \dot{x}_{n-1} \\ \dot{x}_n \end{pmatrix} = \begin{pmatrix} h_{1a} & h_{1b} & \cdots & h_{1(m-1)} & h_{1m} \\ h_{2a} & h_{2b} & \cdots & h_{2(m-1)} & h_{2m} \\ \vdots & \vdots & \ddots & \vdots & \vdots \\ h_{(n-1)a} & h_{(n-1)b} & \cdots & h_{(n-1)(m-1)} & h_{(n-1)m} \\ h_{na} & h_{nb} & \cdots & h_{n(m-1)} & h_{nm} \end{pmatrix} \begin{pmatrix} \dot{x}_a \\ \dot{x}_b \\ \vdots \\ \dot{x}_{m-1} \\ \dot{x}_m \end{pmatrix} \quad (1)$$

$$\begin{pmatrix} f_1 \\ f_2 \\ \vdots \\ f_{n-1} \\ f_n \end{pmatrix} = \begin{pmatrix} h_{1a} & h_{1b} & \cdots & h_{1(m-1)} & h_{1m} \\ h_{2a} & h_{2b} & \cdots & h_{2(m-1)} & h_{2m} \\ \vdots & \vdots & \ddots & \vdots & \vdots \\ h_{(n-1)a} & h_{(n-1)b} & \cdots & h_{(n-1)(m-1)} & h_{(n-1)m} \\ h_{na} & h_{nb} & \cdots & h_{n(m-1)} & h_{nm} \end{pmatrix} \begin{pmatrix} f_a \\ f_b \\ \vdots \\ f_{m-1} \\ f_m \end{pmatrix} \quad (2)$$

Note that, in Expression (1), $x'_1$ to $x'_n$ (n is an integer equal to or greater than 1) represent velocity vectors for deriving a state value of a velocity, $x'_a$ to $x'_m$ (m is an integer equal to or greater than 1) represent vectors whose elements are a reference value and a velocity based on an action of the actuator (a velocity of the movable element of the actuator or a velocity of a member moved by the actuator), and $h_{1a}$ to $h_{nm}$ represent elements of a transformation matrix representing the function. Furthermore, in Expression (2), $f''_1$ to $f''_n$ (n is an integer equal to or greater than 1) represent force vectors for deriving a state value of force, and $f''_a$ to $f''_m$ (m is an integer equal to or greater than 1) represent vectors whose elements are a reference value and force based on an action of the actuator (force of the movable element of the actuator or force of a member moved by the actuator).

By setting the coordinate transformation in the function-specific force/velocity distribution transformation block FT in accordance with the function to be implemented, various operations may be implemented and scaling may be performed.

That is, in the basic principle of the present invention, the function-specific force/velocity distribution transformation block FT "transforms" a variable (variable in the real space) of a single actuator to a variable group (variables in the virtual space) of the entire system expressing the function to be implemented, and distributes the control energy to velocity control energy and force control energy. In other words, the basic principle of the present invention transforms a coordinate space in which the velocity and the force are related to each other into a coordinate space in which the velocity and the force are independent from each other, and then performs an arithmetic operation regarding control of the velocity and the force. Thus, as compared with a case where the control is performed by using the variable (variable in the real space) of the single actuator, the velocity control energy and the force control energy may be given independently.

The ideal force origin block FC is a block that performs arithmetic operations in the domain of the force in accordance with coordinate transformation defined by the function-specific force/velocity distribution transformation block FT. The ideal force origin block FC sets a target value related to force in performing an arithmetic operation based on the coordinate transformation defined by the function-specific force/velocity distribution transformation block FT. The target value is set as a fixed value or a variable value in accordance with a function to be implemented. For example, in a case where the function to be implemented is similar to a function indicated by a reference value, the target value can be set to zero, and in a case where scaling is performed, a value obtained by expanding or reducing information indicating the function to be implemented can be set.

The ideal velocity origin block PC is a block that performs an arithmetic operation in the domain of the velocity in accordance with coordinate transformation defined by the function-specific force/velocity distribution transformation block FT. The ideal velocity origin block PC sets a target value related to a velocity in performing an arithmetic operation based on the coordinate transformation defined by the function-specific force/velocity distribution transformation block FT. The target value is set as a fixed value or a variable value in accordance with a function to be implemented. For example, in a case where the function to be implemented is similar to a function indicated by a reference value, the target value can be set to zero, and in a case where scaling is performed, a value obtained by expanding or reducing information indicating the function to be implemented can be set.

The inverse transformation block IFT is a block that transforms values in the domains of the velocity and the force to values in a domain of an input to the control object system S (for example, voltage values, current values, or the like).

According to such a basic principle, when information regarding a position in the actuator of the control object system S is input to the function-specific force/velocity distribution transformation block FT, the function-specific force/velocity distribution transformation block FT uses information regarding a velocity and force obtained on the basis of the information regarding the position to apply the control rules corresponding to a function in each of the domains of the position and the force. Then, an arithmetic operation of force corresponding to the function is performed in the ideal force origin block FC, an arithmetic operation of a velocity corresponding to the function is performed in the ideal velocity origin block PC, and control energy is allocated to each of the force and the velocity.

Arithmetic operation results in the ideal force origin block FC and the ideal velocity origin block PC are information indicating control targets of the control object system S. These arithmetic operation results are used as input values of the actuator in the inverse transformation block IFT and input to the control object system S.

As a result, the actuator of the control object system S executes an operation in accordance with the function defined by the function-specific force/velocity distribution transformation block FT, and the operation of the device that is the object is implemented.

Furthermore, in a case where a tactile force transmission function involving scaling (amplification of force or a position) is implemented, the coordinate transformation in the function-specific force/velocity distribution transformation block FT in FIG. 2 is represented as the following Expressions (3) and (4).

[Math. 2]

$$\begin{pmatrix} \dot{x}_p \\ \dot{x}_f \end{pmatrix} = \begin{pmatrix} 1 & -\alpha \\ 1 & \beta \end{pmatrix}\begin{pmatrix} \dot{x}_m \\ \dot{x}_s \end{pmatrix} \tag{3}$$

$$\begin{pmatrix} f_p \\ f_f \end{pmatrix} = \begin{pmatrix} 1 & -\alpha \\ 1 & \beta \end{pmatrix}\begin{pmatrix} f_m \\ f_s \end{pmatrix} \tag{4}$$

Note that, in Expression (3), $x'_p$ is a velocity for deriving a state value of a velocity, and $x'_f$ is a velocity related to a state value of force. Furthermore, $x'_m$ is a velocity of a reference value (input from the master device 10) (a differential value of a current position of the master device 10), and x's is a current velocity of the slave device 20 (a differential value of the current position). Furthermore, in Expression (4), $f_p$ is force related to a state value of a velocity, and $f_f$ is force for deriving a state value of force. Furthermore, $f_m$ is force of a reference value (input from the master device 10), and $f_s$ is current force of the slave device 20.

In the case of the coordinate transformation indicated in Expressions (3) and (4), a position of the slave device 20 is multiplied by a (a is a positive number) and transmitted to the master device 10, and force of the slave device 20 is multiplied by β (β is a positive number) and transmitted to the master device 10. In the case of amplifying only the force transmitted from the slave device 20 to the master device 10, it is sufficient that $\alpha=1$ holds and a value of β is set in accordance with the objective.

[Hardware Configuration]

Next, a hardware configuration of a control system in the control system 1 will be described.

Figure 3:
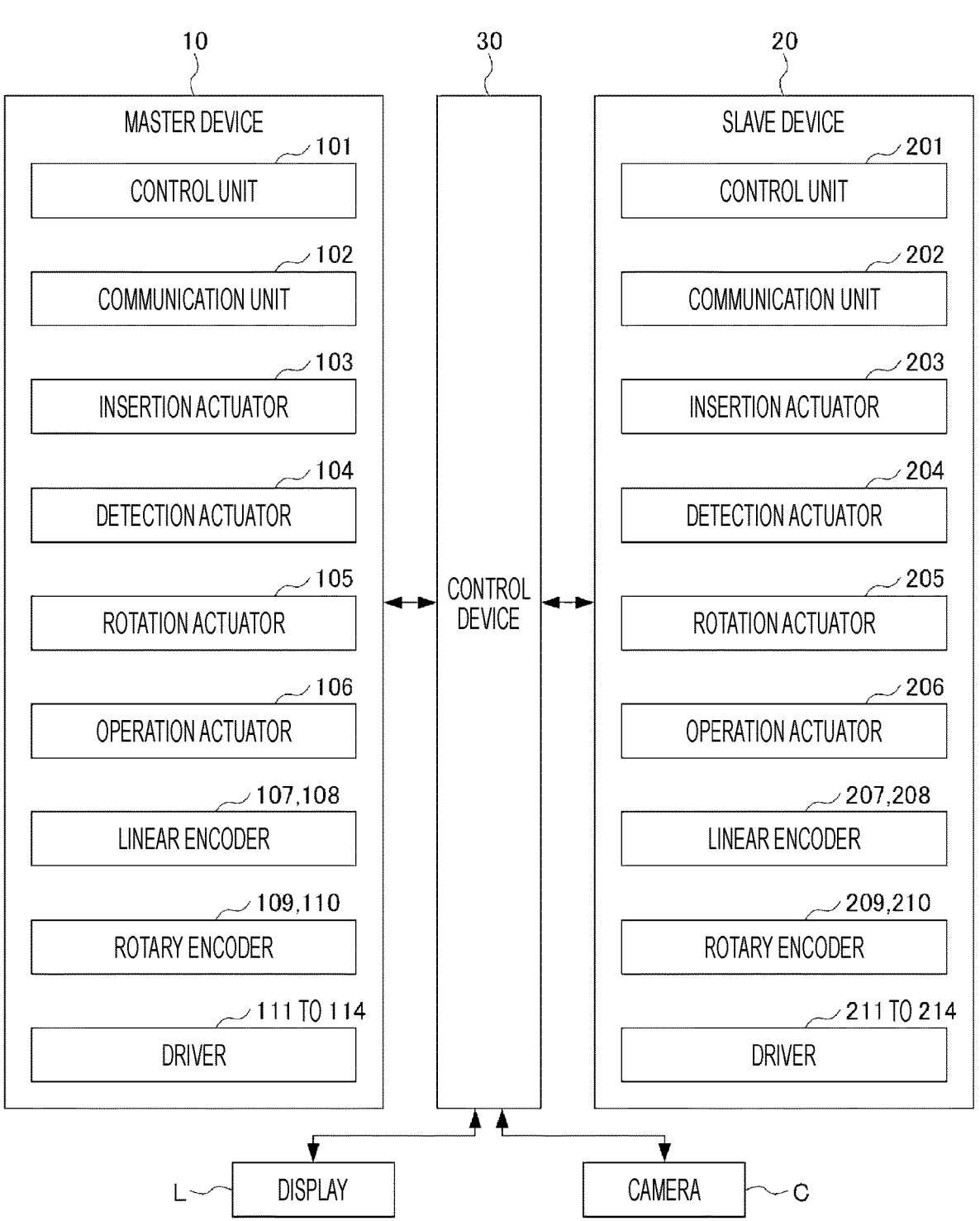
FIG. 3 is a block diagram illustrating a hardware configuration of a control system in the control system 1.

FIG. 3 is a block diagram illustrating the hardware configuration of the control system in the control system 1.

As illustrated in FIG. 3, the control system 1 includes, as the hardware configuration of the control system, the control device 30 including the information processing device such as a PC or a server computer, a control unit 101, a communication unit 102, an insertion actuator 103, a detection actuator 104, a rotation actuator 105, an operation actuator 106, linear encoders 107 and 108, rotary encoders 109 and 110, and drivers 111 to 114 of the master device 10, a control unit 201, a communication unit 202, an insertion actuator 203, a detection actuator 204, a rotation actuator 205, an operation actuator 206, linear encoders 207 and 208, rotary encoders 209 and 210, and drivers 211 to 214 of the slave device 20, the display L, and the cameras C.

The control unit 101 of the master device 10 includes a microcomputer including a processor, a memory, and the like, and controls an operation of the master device 10. For example, the control unit 101 controls driving of the insertion actuator 103, the detection actuator 104, the rotation actuator 105, and the operation actuator 106 of the master device 10 in accordance with control parameters transmitted from the control device 30.

The communication unit 102 controls communication performed by the master device 10 with another device via the network 40.

The insertion actuator 103 includes, for example, a linear motion motor, and applies reaction force to an operation of advancing and retracting the catheter for inserting the catheter into a blood vessel, which is input to the master device 10 by an operator, in accordance with an instruction from the control unit 101.

The detection actuator 104 includes, for example, a voice coil motor, and applies reaction force to an operation of advancing and retracting the catheter for treatment near a lesion, which is input to the master device 10 by an operator, in accordance with an instruction from the control unit 101.

In the present embodiment, the insertion actuator 103 has a longer stroke than the detection actuator 104, while the detection actuator 104 can control a position and force with higher accuracy than the insertion actuator 103.

The rotation actuator 105 includes, for example, a rotary motor, and applies reaction force to an operation of rotating the master device 10 about a rotation axis along an advancing and retracting direction by an operator, in accordance with an instruction from the control unit 101.

The operation actuator 106 includes, for example, a rotary motor, and applies reaction force to an operation input to a lever (grip portion) or the like for operating the end effector by an operator, in accordance with an instruction from the control unit 101.

The linear encoder 107 detects a position (advancing and retracting position on a translation axis) of a movable element of the insertion actuator 103.

The linear encoder 108 detects a position (advancing and retracting position on a translation axis) of a movable element of the detection actuator 104.

The rotary encoder 109 detects a position (rotation angle) of a movable element of the rotation actuator 105.

The rotary encoder 110 detects a position (rotation angle) of a movable element of the operation actuator 106.

The driver 111 outputs a drive current to the insertion actuator 103 in accordance with an instruction from the control unit 101.

The driver 112 outputs a drive current to the detection actuator 104 in accordance with an instruction from the control unit 101.

The driver 113 outputs a drive current to the rotation actuator 105 in accordance with an instruction from the control unit 101.

The driver 114 outputs a drive current to the operation actuator 106 in accordance with an instruction from the control unit 101.

The control unit 201 of the slave device 20 includes a microcomputer including a processor, a memory, and the like, and controls an operation of the slave device 20. For example, the control unit 201 controls driving of the insertion actuator 203, the detection actuator 204, the rotation actuator 205, and the operation actuator 206 of the slave device 20 in accordance with control parameters transmitted from the control device 30.

The communication unit 202 controls communication performed by the slave device 20 with another device via the network 40.

The insertion actuator 203 includes, for example, a linear motion motor, and advances and retracts the catheter of the slave device 20 in accordance with an operation of advancing and retracting the catheter for inserting the catheter into a blood vessel, which is input to the master device 10 by an operator, in accordance with an instruction from the control unit 201.

The detection actuator 204 includes, for example, a voice coil motor, and advances and retracts the catheter of the slave device 20 in accordance with an operation of advancing and retracting the catheter for treatment near a lesion, which is input to the master device 10 by an operator, in accordance with an instruction from the control unit 201.

In the present embodiment, the insertion actuator 203 has a longer stroke than the detection actuator 204, while the detection actuator 204 can control a position and force with higher accuracy than the insertion actuator 203.

The rotation actuator 205 includes, for example, a rotary motor, and rotates the catheter of the slave device 20 about a rotation axis along an advancing and retracting direction in accordance with an operation input to the master device 10 by an operator, in accordance with an instruction from the control unit 201.

The operation actuator 206 includes, for example, a rotary motor, and operates (performs an expansion/contraction operation, an opening/closing operation, and the like on) the end effector in accordance with an operation input to the master device 10 by an operator, in accordance with an instruction from the control unit 201.

The linear encoder 207 detects a position (advancing and retracting position on a translation axis) of a movable element of the insertion actuator 203.

The linear encoder 208 detects a position (advancing and retracting position on a translation axis) of a movable element of the detection actuator 204.

The rotary encoder 209 detects a position (rotation angle) of a movable element of the rotation actuator 205.

The rotary encoder 210 detects a position (rotation angle) of a movable element of the operation actuator 206.

The driver 211 outputs a drive current to the insertion actuator 203 in accordance with an instruction from the control unit 201.

The driver 212 outputs a drive current to the detection actuator 204 in accordance with an instruction from the control unit 201.

The driver 213 outputs a drive current to the rotation actuator 205 in accordance with an instruction from the control unit 201.

The driver 214 outputs a drive current to the operation actuator 206 in accordance with an instruction from the control unit 201.

The display L is installed at a place where an operator of the master device 10 can visually recognize a screen, and displays an image (such as a visible light image or an X-ray image of a subject captured by the camera C) instructed to be displayed by the control device 30.

The camera C is installed at a place where the slave device 20 can capture a subject into which the catheter is inserted, captures an image (such as a visible light image or an X-ray image) of the subject, and transmits the captured image to the control device 30.

Figure 4:
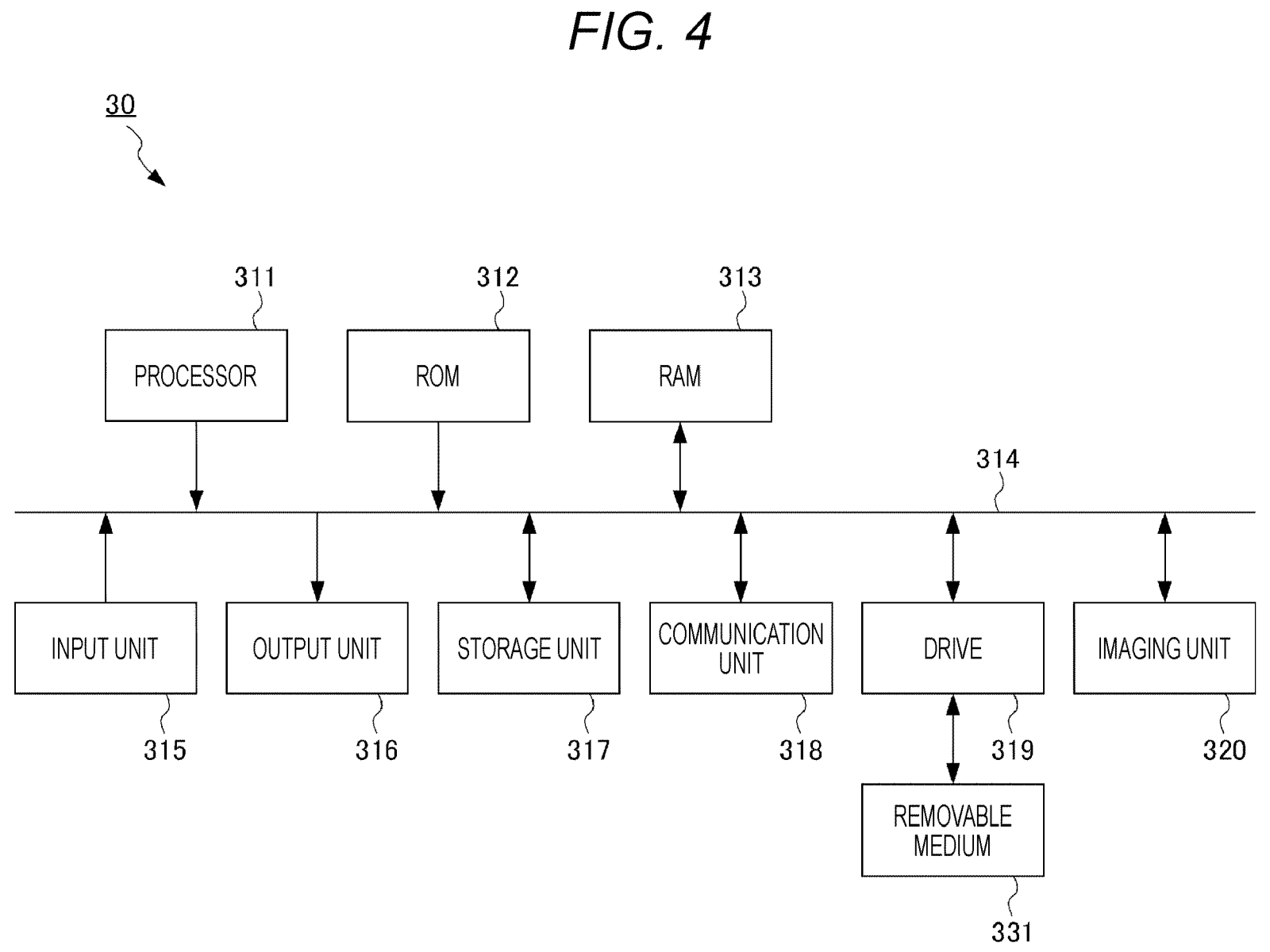

FIG. 4 is a schematic diagram illustrating a hardware configuration of the information processing device constituting the control device 30.

As illustrated in FIG. 4, the control device 30 includes a central processing unit (CPU) 311, a read only memory (ROM) 312, a random access memory (RAM) 313, a bus

314, an input unit 315, an output unit 316, a storage unit 317, a communication unit 318, a drive 319, and an imaging unit 320.

The CPU 311 executes various types of processing in accordance with a program recorded in the ROM 312 or a program loaded from the storage unit 317 to the RAM 313.

The RAM 313 appropriately stores data and the like necessary for the CPU 311 to execute various types of processing.

The CPU 311, the ROM 312, and the RAM 313 are mutually connected via the bus 314. The input unit 315, the output unit 316, the storage unit 317, the communication unit 318, the drive 319, and the imaging unit 320 are connected to the bus 314.

The input unit 315 includes various buttons and the like, and inputs various types of information in accordance with an instruction operation.

The output unit 316 includes a display, a speaker, and the like, and outputs an image and sound.

Note that, in a case where the control device 30 is configured as a smartphone or a tablet terminal, the input unit 315 and the display of the output unit 316 may be arranged in an overlapping manner to configure a touch panel.

The storage unit 317 includes a hard disk, a dynamic random access memory (DRAM), or the like, and stores various types of data managed by each server.

The communication unit 318 controls communication performed by the control device 30 with another device via the network.

A removable medium 331 including a magnetic disk, an optical disk, a magneto-optical disk, a semiconductor memory, or the like is appropriately mounted on the drive 319. A program read from the removable medium 331 by the drive 319 is installed in the storage unit 317 as necessary.

[Functional Configuration]

Next, a functional configuration of the control system 1 will be described.

Figure 5:
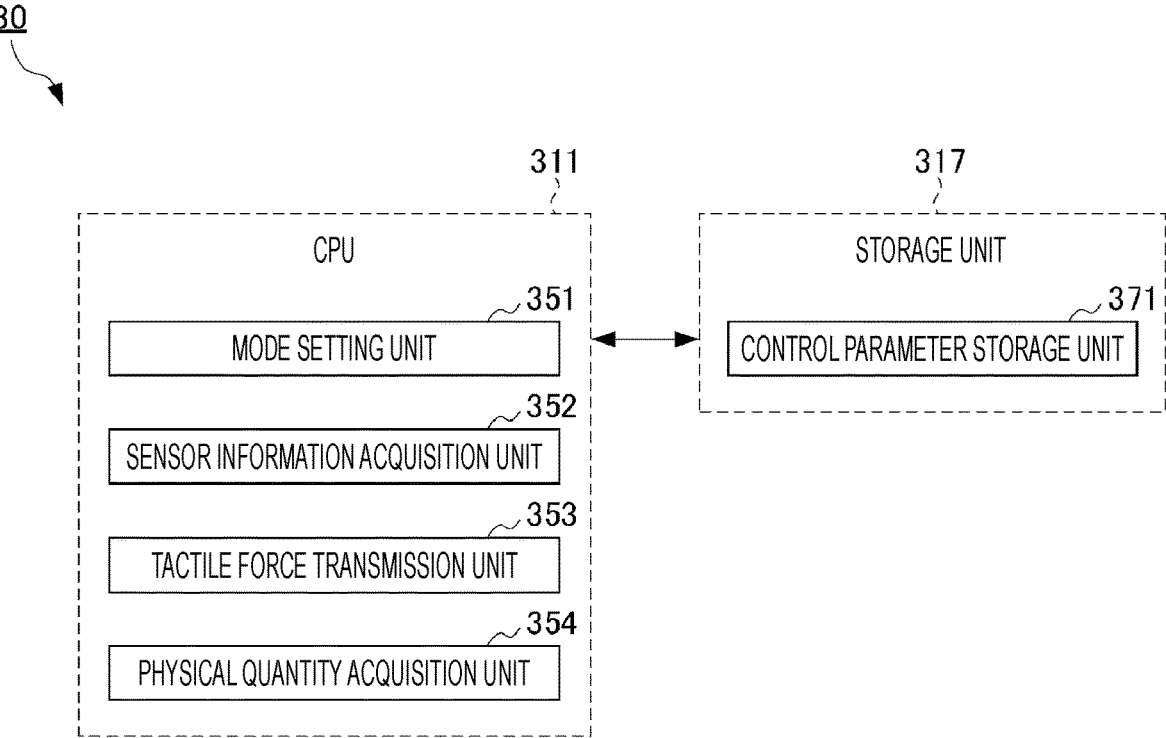
FIG. 5 is a block diagram illustrating a functional configuration of the control system 1.

FIG. 5 is a block diagram illustrating the functional configuration of the control system 1.

As illustrated in FIG. 5, in the control system 1, the control device 30 executes various types of processing, whereby a mode setting unit 351, a sensor information acquisition unit 352, a tactile force transmission unit 353, and a physical quantity acquisition unit 354 function in the CPU 311. Furthermore, a control parameter storage unit 371 is formed in the storage unit 317.

The control parameter storage unit 371 stores, in time series, control parameters acquired in control in which the control device 30 transmits tactile force between the master device 10 and the slave device 20. In the present embodiment, information stored as the control parameters can be various parameters acquired by the tactile force transmission control, and can include various types of information capable of reproducing the tactile force transmission control. For example, sensor information acquired in the master device 10 and the slave device 20, a state value obtained by coordinate transformation of the sensor information, a current command value to each actuator, various setting values set in the control device 30 for the tactile force transmission control, and the like can be stored as the control parameters.

The mode setting unit 351 determines whether or not a physical quantity of the catheter acquired by the physical quantity acquisition unit 354 meets a condition (hereinafter, referred to as a "mode switching condition") set for switching between an insertion mode and a detection mode, and switches between the insertion mode and the detection mode in a case where it is determined that the physical quantity meets the mode switching condition.

The "insertion mode" is a mode for amplifying external force (resistance force) detected in the slave device 20 at a first amplification factor and transmitting tactile force to the master device 10. The "insertion mode" is, for example, a mode set before an operator inserts the catheter into a subject and a distal end of the catheter reaches near a lesion. In the present embodiment, in the "insertion mode", force detected in the slave device 20 is amplified at the first amplification factor that is a relatively small amplification factor, and transmitted to the master device 10. The first amplification factor can be set on the basis of, for example, a measured value, a statistic, an estimated value obtained by simulation, or the like in accordance with a configuration of the catheter, physical characteristics of a subject (a thickness of a blood vessel, and the like), a length of the catheter to be inserted, and the like.

The "detection mode" is a mode for amplifying external force (resistance force) detected in the slave device 20 at a second amplification factor larger than the first amplification factor and transmitting tactile force to the master device 10. The "detection mode" is, for example, a mode set after an operator inserts the catheter into a subject and the distal end of the catheter reaches near a lesion. In the present embodiment, in the "detection mode", force detected in the slave device 20 is amplified at the second amplification factor that is a relatively large amplification factor, and transmitted to the master device 10.

Therefore, in the "detection mode", an operator can more sharply sense the external force input to the slave device 20 than in the "insertion mode".

Note that, hereinafter, a section in which it is determined that it is appropriate to sharply transmit tactile force of the catheter near a lesion is appropriately referred to as a "specific section".

Here, as the mode switching condition, for example, it is possible to set that switching of the mode is manually instructed by an operation of a user or that the physical quantity for determining the mode switching condition meets the set condition (resistance force input to the catheter has changed by equal to or greater than a threshold, a distance between the distal end of the catheter and a lesion has fallen within the threshold, or the like). As an example, in a case where it is determined in the insertion mode that the distance between the distal end of the catheter of the slave device 20 and the lesion has fallen within the threshold, the insertion mode can be switched to the detection mode. Furthermore, in a case where it is determined in the detection mode that the distance between the distal end of the catheter of the slave device 20 and the lesion is equal to or greater than the threshold, the detection mode can be switched to the insertion mode.

The sensor information acquisition unit 352 acquires information (sensor information) detected by various sensors installed in the master device 10 and the slave device 20. For example, the sensor information acquisition unit 352 acquires information indicating the positions (the advancing and retracting positions or the rotation angles) of the movable elements of the actuators detected by the linear encoders 107, 108, 207, and 208 and the rotary encoders 109, 110, 209, and 210. Furthermore, the sensor information acquisition unit 352 stores the acquired sensor information in the control parameter storage unit 371 as time-series data.

The tactile force transmission unit 353 controls tactile force transmission in the master device 10 and the slave device 20 in accordance with the control algorithm illustrated in FIG. 2. For example, the tactile force transmission unit 353 executes control to transmit tactile force between the actuators for corresponding operations of the master device 10 and the slave device 20 in tactile force transmission processing. At this time, the tactile force transmission unit 353 amplifies external force detected in the slave device 20 at an amplification factor set by the mode setting unit 351, and transmits the amplified external force to the master device 10. Note that, as described above, information regarding a position (a position, a velocity, or the like) can be either amplified and transmitted from the slave device 20 to the master device 10 or directly transmitted without being amplified.

The physical quantity acquisition unit 354 acquires a physical quantity (resistance force input to the catheter, a distance between the distal end of the catheter and a lesion, or the like) for determining the condition (mode switching condition) related to the mode in the tactile force transmission processing.

For example, the physical quantity acquisition unit 354 reads time-series control parameters stored in the control parameter storage unit 371, and calculates resistance force input from the outside to the catheter of the slave device 20. In a case where the catheter is inserted into a subject, for example, the resistance force changes between a state where the catheter advances in an artery and a state where the catheter reaches a stenosed lesion site of a heart or the like. The physical quantity acquisition unit 354 calculates the resistance force input from the outside to the catheter of the slave device 20, thereby making it possible to determine the insertion state of the catheter. Note that the physical quantity acquisition unit 354 can acquire, as the physical quantity, an instantaneous value, a value obtained by an arithmetic operation such as a moving average, or the like. Furthermore, the physical quantity acquisition unit 354 may acquire the physical quantity for determining the mode switching condition after performing filter processing (band limiting filter) on a waveform of the instantaneous value of the physical quantity.

Furthermore, the physical quantity acquisition unit 354 calculates a distance between the distal end of the catheter and a lesion on the basis of an image captured by the camera C. By calculating the distance between the distal end of the catheter and the lesion from the image captured by the camera C, it is possible to determine approach of the catheter to the lesion on the basis of a criterion similar to that of a case where a human visually determines the approach. Note that, in the case of acquiring the distance between the distal end of the catheter and the lesion, various sensors can be used. For example, a marker for magnetic detection may be provided at the distal end of the catheter, and a position of the catheter may be detected by a magnetic sensor from the outside of the subject to acquire the distance to the lesion. Furthermore, a sensor for detecting a distal end position of the catheter may be installed in advance inside the subject, and the distal end position of the catheter may be detected by the sensor to acquire the distance to the lesion.

[Setting of Amplification Factor]

As described above, in the present embodiment, the detection mode is set at a position (specific section) close to an object site (lesion) to be treated with the catheter, and force detected in the slave device 20 is amplified at the second amplification factor and transmitted to the master device 10. Furthermore, the insertion mode is set at a position away from the object site (lesion) to be treated with the catheter, and force detected in the slave device 20 is amplified at the first amplification factor and transmitted to the master device 10.

The second amplification factor set in the detection mode can be set on the basis of a boundary value (threshold) that makes it easy for a human to perceive a change in force (tactile force).

As an example, in a case where the first amplification factor in the insertion mode is k1 and the second amplification factor in the detection mode is k2, it is sufficient that k2 that satisfies Dth/D=k2/k1 is set in order to set a change rate D of the force amplified by the first amplification factor k1 as a threshold Dth related to the change rate of the force.

That is, in an environment where a maximum value of a change rate of force input to the catheter near the lesion (specific section) is Dmax (<Dth) in a state where the force detected in the slave device 20 is amplified at the first amplification factor k1 in the insertion mode, an operator can sense a change in the force equal to or greater than the threshold Dth related to the change rate of the force by setting the second amplification factor k2=(Dth/Dmax)·k1 in the detection mode.

In order to set the second amplification factor k2 in this manner, for example, it is useful to cause the catheter to enter near the lesion (specific section) in advance in a state where the insertion mode is set and to detect the change rate of the force. Alternatively, the second amplification factor k2 may be set on the basis of a statistic or an estimated value obtained by simulation.

[Operation]

Next, an operation of the control system 1 will be described.

[Tactile Force Transmission Processing]

Figure 6:
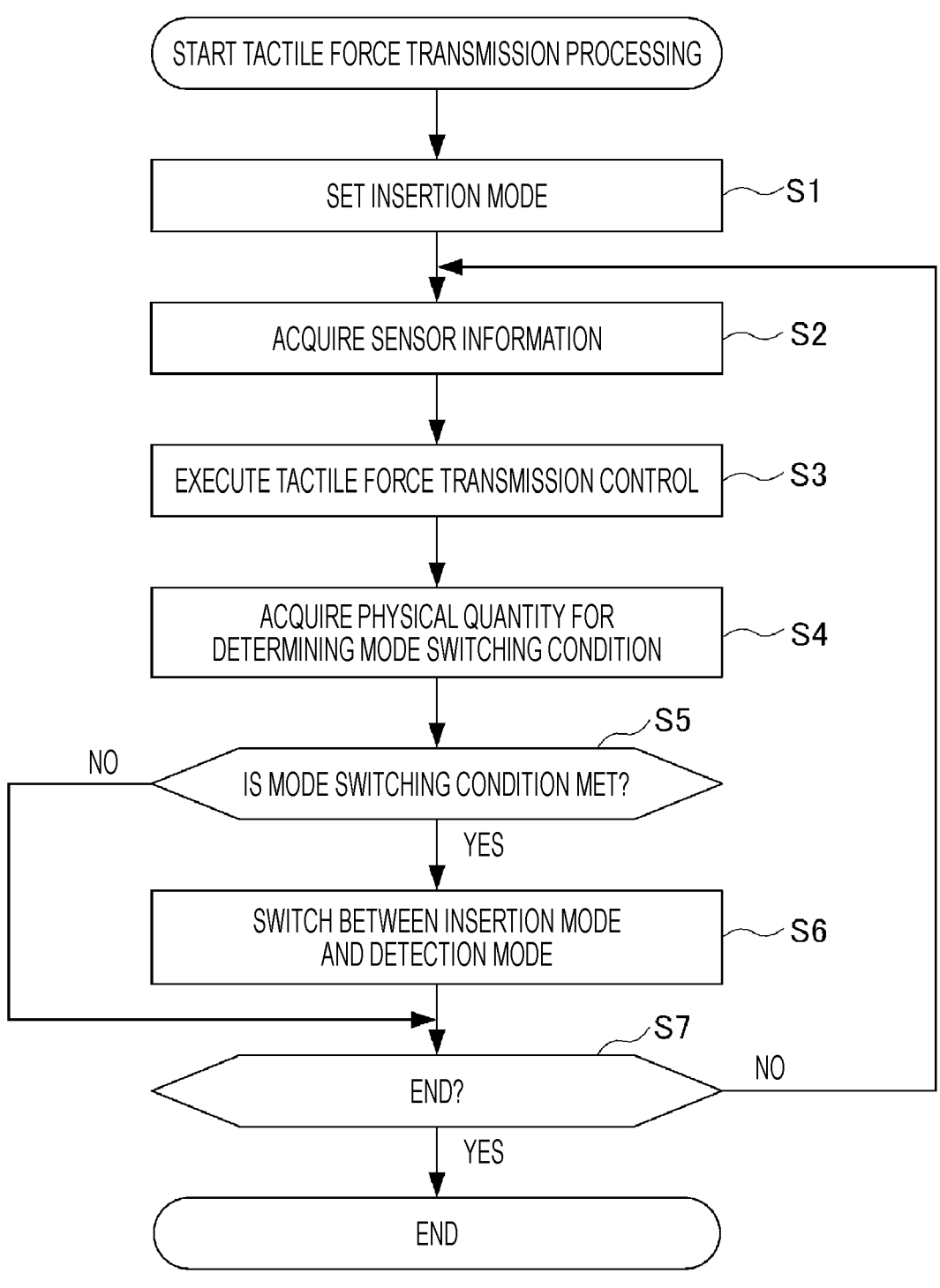
FIG. 6 is a flowchart for describing a flow of tactile force transmission processing executed by the control device 30.

FIG. 6 is a flowchart for describing a flow of the tactile force transmission processing executed by the control device 30.

The tactile force transmission processing is started in response to an instruction to execute the tactile force transmission processing via the input unit 315 or the communication unit 318. In the present embodiment, in a case where the tactile force transmission processing is started, it is assumed that the processing is started in a state where the distal end of the catheter is inserted into a subject by a predetermined distance (for example, a state where about 1 to 10 [cm] is inserted) manually by an operator assisting an operation of the slave device 20 or by a remote operation from the master device 10. With this configuration, it is possible to suppress control of the control device 30 from becoming unstable in a state where a change in external force at an initial stage of the insertion is large.

In step S1, the mode setting unit 351 sets the mode for transmitting tactile force to the insertion mode. With this configuration, an amplification factor of force fed back from the slave device 20 to the master device 10 is set to the first amplification factor.

In step S2, the sensor information acquisition unit 352 acquires information (sensor information) detected by various sensors installed in the master device 10 and the slave device 20. The sensor information acquired in step S2 is stored in the control parameter storage unit 371 as time-series data.

In step S3, the tactile force transmission unit 353 executes the tactile force transmission control on the basis of the sensor information while amplifying the external force detected in the slave device 20 at the first amplification factor.

In step S4, the physical quantity acquisition unit 354 acquires a physical quantity (resistance force input to the catheter, a distance between the distal end of the catheter and a lesion, or the like) for determining the mode switching condition.

In step S5, the mode setting unit 351 determines whether or not the acquired physical quantity meets the mode switching condition set for switching between the insertion mode and the detection mode. Specifically, the mode setting unit 351 determines whether or not switching of the mode is manually instructed by an operation of a user or whether or not the physical quantity for determining the mode switching condition meets the set condition (whether or not resistance force input to the catheter has changed by equal to or greater than a threshold, whether or not a distance between the distal end of the catheter and a lesion has fallen within the threshold, or the like).

In a case where the acquired physical quantity does not meet the mode switching condition set for switching between the insertion mode and the detection mode, NO is determined in step S5, and the processing proceeds to step S7.

On the other hand, in a case where the acquired physical quantity meets the mode switching condition set for switching between the insertion mode and the detection mode, YES is determined in step S5, and the processing proceeds to step S6.

In step S6, the mode setting unit 351 switches between the insertion mode and the detection mode. That is, the mode setting unit 351 switches to the detection mode in a case where the insertion mode is set, and switches to the insertion mode in a case where the detection mode is set.

In step S7, the tactile force transmission unit 353 determines whether or not end of the tactile force transmission processing is instructed.

In a case where the end of the tactile force transmission processing is not instructed, NO is determined in step S7, and the processing proceeds to step S2.

On the other hand, in a case where the end of the tactile force transmission processing is instructed, YES is determined in step S7, and the tactile force control processing ends.

[Verification of Effect]

Figure 7:
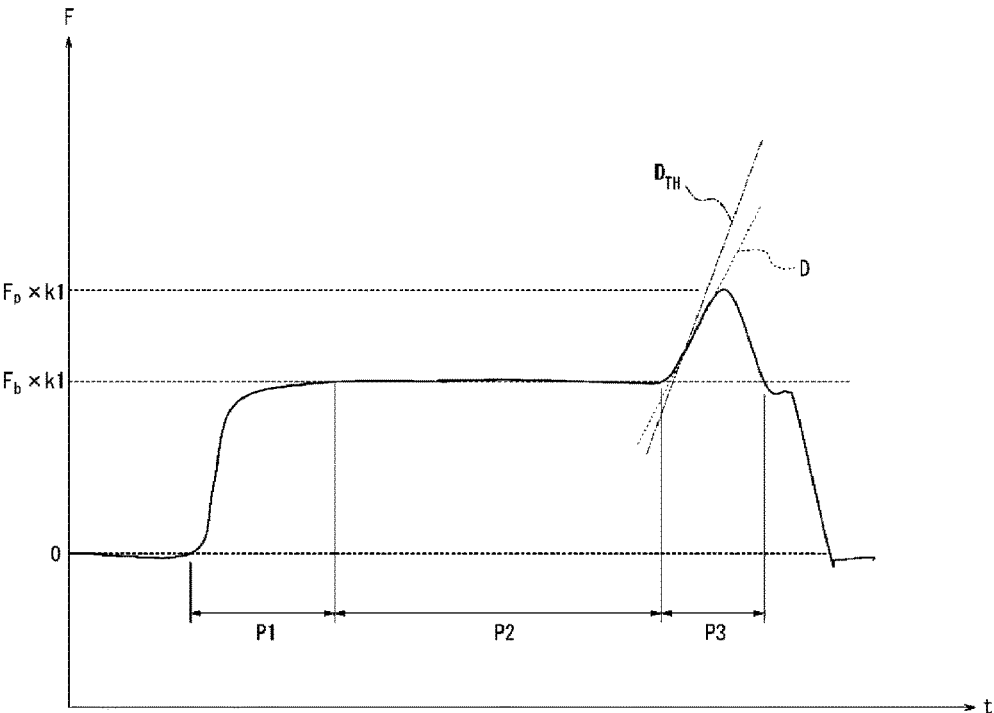
FIG. 7 is a schematic diagram illustrating a temporal change in magnitude of force fed back from a slave device 20 to a master device 10 in a case where an amplification factor is constant.

FIG. 7 is a schematic diagram illustrating a temporal change in magnitude of force fed back from the slave device 20 to the master device 10 in a case where an amplification factor is constant.

Note that FIG. 7 illustrates the magnitude of the force when the force is fed back to the master device 10 with the amplification factor constant in a case where an operator operates the master device 10 to insert the catheter of the slave device 20 into a subject. In FIG. 7, it is assumed that an amplification factor for amplifying external force (resistance force) detected in the slave device 20 is k1 (constant). Furthermore, in FIG. 7, a horizontal axis represents time, and a vertical axis represents the magnitude of the force fed back to the operator.

In a period P1, the catheter starts to move with start of the operation, and the external force (resistance force) detected in the slave device 20 increases.

In a period P2, the catheter of the slave device 20 advances in a stationary environment (such as in an artery) in the subject, and the resistance force including a dynamic friction force from an inner wall of a blood vessel or the like acts with substantially constant magnitude $F_b$. In the period P2, the force fed back from the slave device 20 to the master device 10 is represented as $F_b \times k1$.

In a period P3, the catheter of the slave device 20 comes into contact with a lesion or the like in the subject, so that acceleration is generated (resistance force is increased). In the period P3, a maximum value of the force input to the slave device 20 is $F_p$, and a maximum value of the force fed back from the slave device 20 to the master device 10 is represented as $F_p \times k1$.

Here, in the example illustrated in FIG. 7, in the period P3, a maximum value of the change rate D of the force fed back to the master device 10 is smaller than the threshold Dth related to the change rate of the force.

In this case, it is difficult for a user to perceive the change in the force (tactile force) fed back from the slave device 20 to the master device 10, and there is a possibility that the user cannot perform an appropriate operation.

Figure 8:
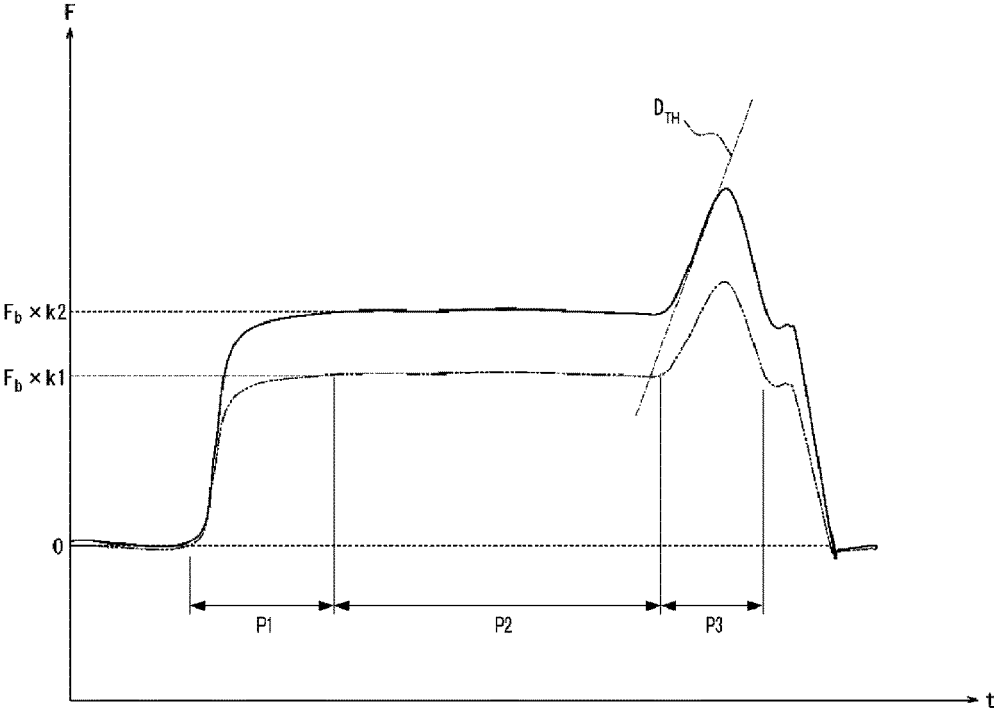
FIG. 8 is a schematic diagram illustrating a temporal change in the magnitude of the force fed back from the slave device 20 to the master device 10 in a case where the amplification factor is increased as compared with the example illustrated in FIG. 7.

FIG. 8 is a schematic diagram illustrating a temporal change in the magnitude of the force fed back from the slave device 20 to the master device 10 in a case where the amplification factor is increased as compared with the example illustrated in FIG. 7.

Note that FIG. 8 illustrates the magnitude of the force when the amplification factor k2 larger than the amplification factor k1 in FIG. 7 is set and the force is fed back to the master device 10 in a case where the operator operates the master device 10 to insert the catheter of the slave device 20 into the subject. In FIG. 8, for reference, the magnitude of the force in the case of amplification with the amplification factor k1 is indicated by a two-dot chain line. Furthermore, in FIG. 8, a horizontal axis represents time, and a vertical axis represents the magnitude of the force fed back to the operator.

In the period P1, the catheter starts to move with start of the operation, and the external force (resistance force) detected in the slave device 20 increases.

In the period P2, the catheter of the slave device 20 advances in the stationary environment (such as in the artery) in the subject, and the resistance force including the dynamic friction force from the inner wall of the blood vessel or the like acts with the substantially constant magnitude. In the period P2, the force fed back from the slave device 20 to the master device 10 is represented as $F_b \times k2$.

In the period P3, the catheter of the slave device 20 comes into contact with the lesion or the like in the subject, so that the acceleration is generated (resistance force is increased).

Here, in the example illustrated in FIG. 8, in the period P3, a maximum value of the change rate D of the force fed back to the master device 10 is equal to the threshold Dth related to the change rate of the force.

In this case, a user can easily perceive the change in the force (tactile force) fed back from the slave device 20 to the master device 10, and can perform an appropriate operation.

In the control system 1 in the present embodiment, control is performed such that the force fed back from the slave device 20 to the master device 10 is amplified at the amplification factor k1 until the period P2, and the force fed back from the slave device 20 to the master device 10 is increased to the amplification factor k2 in the period P3.

Figure 9:
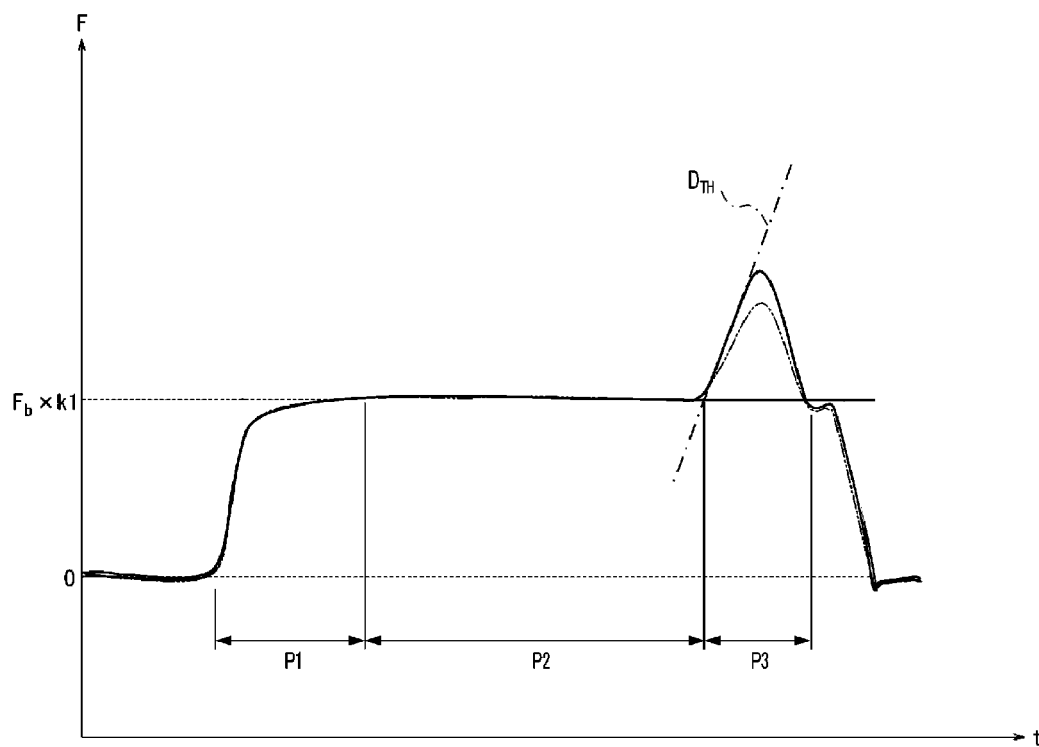
FIG. 9 is a schematic diagram illustrating a temporal change in the magnitude of the force fed back from the slave device 20 to the master device 10 in a case where the amplification factor of the force is increased in a period P3.

FIG. 9 is a schematic diagram illustrating a temporal change in the magnitude of the force fed back from the slave device 20 to the master device 10 in a case where the amplification factor of the force is increased in the period P3. In FIG. 9, for reference, the magnitude of the force in the case of amplification with the amplification factor k1 is indicated by a two-dot chain line. Furthermore, in FIG. 9, a horizontal axis represents time, and a vertical axis represents the magnitude of the force fed back to the operator.

As illustrated in FIG. 9, in the present embodiment, it is possible to provide the control system 1 that makes it possible to easily perceive the change in the force in a specific section (near a lesion) and perform an appropriate operation while suppressing the resistance force felt during insertion of the catheter by setting the insertion mode and feeding back the force from the slave device 20 to the master device 10 at the first amplification factor k1 in the period P2, and setting the detection mode and feeding back the force from the slave device 20 to the master device 10 at the second amplification factor k2 in the period P3.

[First Modification]

In the embodiment described above, the configuration has been described as an example in which the actuator operates after the catheter is inserted until the catheter reaches a lesion, but the present invention is not limited thereto. For example, the catheter may be manually inserted to near the lesion, and force may be fed back from the slave device 20 to the master device 10 in a specific section near the lesion. In this case, an operator can manually insert the catheter of the slave device 20 to near the lesion, initially feed back the force at the first amplification factor near the lesion, and switch to the second amplification factor at a position (specific section) closer to the lesion.

Figure 10:
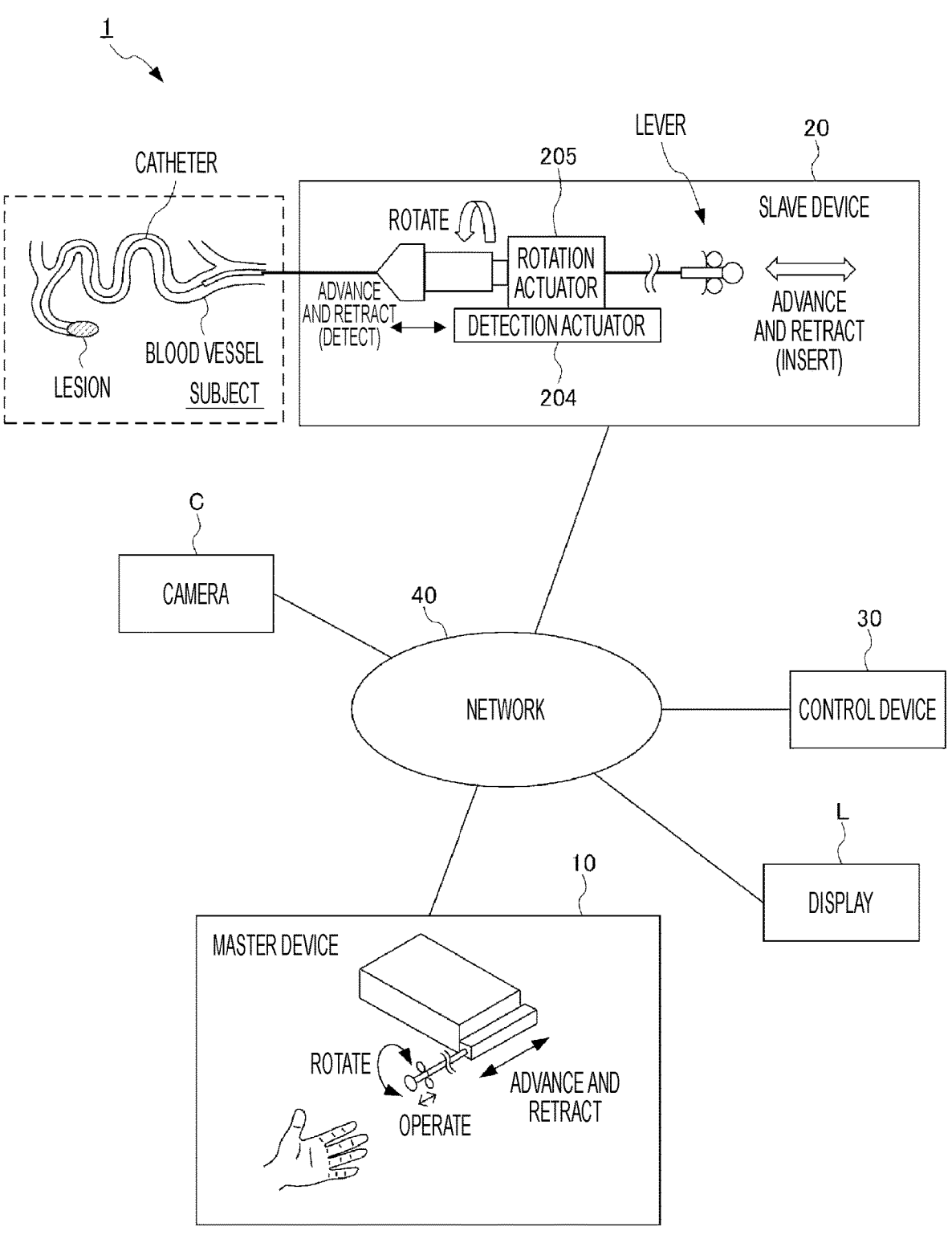
FIG. 10 is a schematic diagram illustrating a configuration of the control system 1 that performs feedback of force after an operator manually inserts a catheter of the slave device 20.

FIG. 10 is a schematic diagram illustrating a configuration of the control system 1 that performs feedback of force after an operator manually inserts the catheter of the slave device 20.

As illustrated in FIG. 10, in the control system 1 of the present modification, a lever (grip portion) or the like for operation is installed in the catheter of the slave device 20, and a manual operation by an operator is possible.

Furthermore, the control system 1 of the present modification includes only the detection actuators 104 and 204 and does not include the insertion actuators 103 and 203 among the linear motion actuators included in the control system 1 of the first embodiment illustrated in FIG. 1.

In a case where the operator manually inserts the catheter, in the slave device 20, the catheter is released from movement control by the detection actuator 204 and the rotation actuator 205, and can be operated in a similar manner to the conventional catheter.

At this time, it is assumed that the catheter is inserted to a position in front of near the lesion by the operator, and the tactile force transmission processing is started with this state as an initial state.

In a case where the tactile force transmission processing is started, the catheter is held for movement control by the detection actuator 204 and the rotation actuator 205, the slave device 20 moves the catheter in accordance with an operation on the master device 10, and external force input to the catheter is fed back from the slave device 20 to the master device 10.

In the tactile force transmission processing of the present modification, similarly to the first embodiment, the insertion mode is initially set, and the external force input to the slave device 20 is amplified at the first amplification factor and transmitted to the master device 10.

Then, in a case where it is determined that the physical quantity for determining the mode switching condition meets the mode switching condition set for switching between the insertion mode and the detection mode, the detection mode is set, and the external force input to the slave device 20 is amplified at the second amplification factor and transmitted to the master device 10.

In the present modification, since a distance for moving the catheter by the actuator is relatively short, it is sufficient to provide an actuator having a short stroke such as a voice coil motor.

In this manner, also in a case where the catheter is inserted into a subject by the control system 1 of the present modification, similarly to the control system 1 of the first embodiment, it is possible to switch an amplification factor of force fed back from the slave device 20 to the master device 10 from the first amplification factor to the second amplification factor near a lesion.

Therefore, it is possible to transmit tactile force input from the outside to the slave device 20 to the master device 10 so that the tactile force can be more easily perceived.

OTHER MODIFICATIONS

In the embodiment described above, the description has been made assuming that the force in the thrust direction (advancing and retracting direction) of the catheter is subjected to tactile force transmission between the master device 10 and the slave device 20, but the present invention is not limited thereto. For example, the force related to the rotation about the rotation axis along the advancing and retracting direction or the operation of the end effector may be subjected to the tactile force transmission between the master device 10 and the slave device 20. Furthermore, in this case, switching may be performed such that the amplification factor of the force fed back from the slave device 20 to the master device 10 is increased in a specific section to perform the tactile force transmission.

Furthermore, in the embodiment described above, the description has been made assuming that the amplification factor of the force fed back from the slave device 20 to the master device 10 is set in two stages of the first amplification factor and the second amplification factor, but the present invention is not limited thereto. That is, more than two types of modes of the insertion mode and the detection mode may be set, equal to or greater than three stages of amplification factors corresponding to these modes may be set, and the force may be fed back from the slave device 20 to the master device 10.

Furthermore, in the embodiment described above, the second amplification factor in the specific section may be set as a function reflecting the change in the resistance force input to the catheter. With this configuration, the force fed back from the slave device 20 to the master device 10 can be amplified by adaptively reflecting the change in the resistance force input to the catheter.

Furthermore, in the embodiment described above, the description has been made assuming that the second amplification factor in the specific section is set such that the change rate of the force is equal to or greater than the set threshold, but the present invention is not limited thereto. That is, the second amplification factor in the specific section may be set such that a change quantity in the force is equal to or greater than the set threshold.

Furthermore, in the embodiment described above, the case has been described as an example where the actuator included in the master device 10 and the actuator included in the slave device 20 are associated on a one-to-one basis to perform transmission of tactile force, but the present invention is not limited thereto. That is, a plurality of actuators of the master device 10 can be associated with one actuator of the slave device 20 to transmit tactile force, or one actuator of the master device 10 can be associated with a plurality of actuators of the slave device 20 to transmit tactile force. Furthermore, a plurality of actuators of the master device 10 can be associated with a plurality of actuators of the slave device 20 to transmit tactile force. As an example, the insertion actuator 203 and the detection actuator 204 of the slave device 20 illustrated in FIG. 3 can be associated with the insertion actuator 103 of the master device 10 to transmit tactile force. In this case, it is not necessary to provide the detection actuator 104 of the master device 10, and cost reduction, weight reduction of the device, and the like can be implemented.

Furthermore, in the embodiment described above, the configuration including the insertion actuator 203 and the detection actuator 204 as the actuators for advancing and retracting the catheter of the slave device 20 has been described as an example, but the present invention is not limited thereto. That is, the catheter of the slave device 20 may be advanced and retracted by one actuator as long as the actuator satisfies the required performance in a stroke and accuracy of an operation.

As described above, the control system 1 according to the present embodiment includes the master device 10, the slave device 20, and the control device 30. Furthermore, the control device 30 includes the tactile force transmission unit 353 and the mode setting unit 351.

The tactile force transmission unit 353 controls tactile force transmission in the master device 10 and the slave device 20.

The mode setting unit 351 changes an amplification factor of force transmitted from the slave device 20 to the master device 10 in a specific section in which a moving element of the slave device 20 moves on the basis of a physical quantity in the moving element of the slave device 20.

With this configuration, it is possible to implement a control system that makes it possible to easily perceive a change in the force in the specific section (for example, near a lesion or the like) and perform an appropriate operation.

The specific section is a section determined by a distance from an object to which the moving element of the slave device 20 reaches.

The mode setting unit 351 changes the amplification factor in a case where the distance from the object as the physical quantity is within a set threshold.

With this configuration, it is possible to determine approach of the moving element of the slave device 20 to the object on the basis of a criterion similar to that of a case where a human visually determines the approach, and to set an appropriate amplification factor.

The specific section is a section determined by a change in external force input in a path to the object to which the moving element of the slave device 20 reaches.

The mode setting unit 351 changes the amplification factor in a case where the change in the external force as the physical quantity is equal to or greater than a set threshold.

With this configuration, it is possible to determine approach of the moving element of the slave device 20 to the object on the basis of a change in an environment of the path on which the moving element moves, and to set an appropriate amplification factor.

The mode setting unit 351 sets the amplification factor such that a change rate of the force transmitted from the slave device 20 to the master device 10 is equal to or greater than a set threshold in the specific section.

With this configuration, from a viewpoint of the change rate of the force, it is possible to set the amplification factor on the basis of a boundary value (threshold) that makes it easy for a human to perceive the change in the force (tactile force).

The mode setting unit 351 sets the amplification factor such that a change quantity of the force transmitted from the slave device 20 to the master device 10 is equal to or greater than a set threshold in the specific section.

With this configuration, from a viewpoint of the change quantity of the force, it is possible to set the amplification factor on the basis of a boundary value (threshold) that makes it easy for a human to perceive the change in the force (tactile force).

Note that the present invention is not limited to the embodiment described above, and modification, improvement, and the like within a range in which the object of the present invention can be achieved are included in the present invention.

For example, the present invention can be implemented not only as the control system 1 in the embodiment described above, but also as a control device that controls the control system 1, a control method including each step executed in the control system 1, or a program executed by a processor to implement the functions of the control system 1.

Furthermore, in the embodiment described above, the configuration has been described as an example in which the control device 30 is implemented as an independent device, but the functions of the control device 30 can be mounted on one of the control unit 101 of the master device 10 and the control unit 201 of the slave device 20, or can be mounted in a distributed manner on both of them.

Furthermore, the processing in the embodiment described above can be executed by either hardware or software.

That is, it is sufficient that the control system 1 has a function capable of executing the processing described above, and what functional configuration and hardware configuration are used to implement this function is not limited to the examples described above.

In a case where the processing described above is executed by software, a program constituting the software is installed in a computer from a network or a storage medium.

The storage medium storing the program includes a removable medium distributed separately from the device main body, a storage medium incorporated in the device main body in advance, or the like. The removable medium includes, for example, a semiconductor memory, a magnetic disk, an optical disk, a magneto-optical disk, or the like. The optical disk includes, for example, a compact disk-read only memory (CD-ROM), a digital versatile disk (DVD), a Blu-ray (registered trademark) disc, or the like. The magneto-optical disk includes a mini-disk (MD) or the like. Furthermore, the storage medium incorporated in the device main body in advance includes, for example, a read only memory (ROM) or a hard disk in which the program is stored, a semiconductor memory, or the like.

Note that the embodiment described above indicates an example to which the present invention is applied, and does not limit a technical scope of the present invention. That is, the present invention can be subjected to various changes such as omission and replacement without departing from the gist of the present invention, and various embodiments other than the embodiment described above can be taken. Various embodiments and modification thereof that can be taken by the present invention are included in the invention described in the claims and an equivalent scope thereof.

The invention claimed is:

1. A control system including: a master device to which an operation of an operator is input, the master device comprising an actuator; and a slave device that operates in accordance with the operation input to the master device, the slave device comprising an actuator, the control system comprising:

a control device configured to:

control transmission of tactile force in the master device and the slave device by using the actuator of the master device and the actuator of the slave device; and change an amplification factor of force transmitted from the slave device to the master device in a specific section in which a movable element of the slave device moves, on the basis of a physical quantity in the movable element of the slave device, wherein the specific section is a section in which distance between the movable element and a lesion is within a set threshold of distance.

2. The control system according to claim 1, wherein the specific section is a section determined by a distance from an object to which the movable element of the slave device reaches, and the control device is configured to change the amplification factor in a case where the distance from the object as the physical quantity is within the set threshold of distance.

3. The control system according to claim 1, wherein the specific section is a section determined by a change in external force input in a path to an object to which the movable element of the slave device reaches, and the control device is configured to change the amplification factor in a case where the change in the external force as the physical quantity is equal to or greater than a set threshold of force.

4. The control system according to claim 1, wherein the control device is configured to set the amplification factor such that a change rate of the force transmitted from the slave device to the master device is equal to or greater than a set threshold of change rate in the specific section.

5. The control system according to claim 1, wherein the control device is configured to set the amplification factor such that a change quantity of the force transmitted from the slave device to the master device is equal to or greater than a set threshold of change quantity in the specific section.

6. A control device configured to:

control transmission of tactile force in a master device to which an operation of an operator is input, the master device comprising an actuator, and a slave device that operates in accordance with the operation input to the master device, the slave device comprising an actuator, the control device comprising change an amplification factor of force transmitted from the slave device to the master device in a specific section in which a movable element of the slave device moves, on the basis of a physical quantity in the movable element of the slave device, wherein the specific section is a section in which distance between the movable element and a lesion is within a set threshold of distance.

7. A control method executed by a control system including: a master device to which an operation of an operator is input, the master device comprising an actuator; and a slave device that operates in accordance with the operation input to the master device, the slave device comprising an actuator, the control method comprising:

controlling transmission of tactile force in the master device and the slave device; and changing an amplification factor of force transmitted from the slave device to the master device in a specific section in which a movable element of the slave device moves, on the basis of a physical quantity in the movable element of the slave device, wherein the specific section is a section in which distance between the movable element and a lesion is within a set threshold of distance.

8. The control system according to claim 2, wherein the control device is configured to set the amplification factor such that a change rate of the force transmitted from the slave device to the master device is equal to or greater than a set threshold of change rate in the specific section.

9. The control system according to claim 3, wherein the control device is configured to set the amplification factor such that a change rate of the force transmitted from the slave device to the master device is equal to or greater than a set threshold of change rate in the specific section.

10. The control system according to claim 2, wherein the control device is configured to set the amplification factor such that a change quantity of the force transmitted from the slave device to the master device is equal to or greater than a set threshold of change quantity in the specific section.

11. The control system according to claim 3, wherein the control device is configured to set the amplification factor such that a change quantity of the force transmitted from the slave device to the master device is equal to or greater than a set threshold of change quantity in the specific section.

12. The control device according to claim 6, wherein
the specific section is a section determined by a distance from an object to which the movable element of the slave device reaches, and
the control device is configured to change the amplification factor in a case where the distance from the object as the physical quantity is within the set threshold of distance.

13. The control device according to claim 6, wherein
the specific section is a section determined by a change in external force input in a path to an object to which the movable element of the slave device reaches, and the control device is configured to change the amplification factor in a case where the change in the external force as the physical quantity is equal to or greater than a set threshold of force.

14. The control device according to claim 6, wherein the control device is configured to set the amplification factor such that a change rate of the force transmitted from the slave device to the master device is equal to or greater than a set threshold of change rate in the specific section.

15. The control device according to claim 6, wherein the control device is configured to set the amplification factor such that a change quantity of the force transmitted from the slave device to the master device is equal to or greater than a set threshold of change quantity in the specific section.

16. The control method according to claim 7, wherein
the specific section is a section determined by a distance from an object to which the movable element of the slave device reaches, and
the amplification factor is changed, in a case where the distance from the object as the physical quantity is within a set threshold of distance.

17. The control method according to claim 7, wherein
the specific section is a section determined by a change in external force input in a path to an object to which the movable element of the slave device reaches, and
the amplification factor is changed, in a case where the change in the external force as the physical quantity is equal to or greater than a set threshold of force.

18. The control method according to claim 7, wherein the amplification factor is set, such that a change rate of the force transmitted from the slave device to the master device is equal to or greater than a set threshold of change rate in the specific section.

19. The control method according to claim 7, wherein the amplification factor is set, such that a change quantity of the force transmitted from the slave device to the master device is equal to or greater than a set threshold of change quantity in the specific section.

\* \* \* \* \*